United States Patent [19]

Hickle et al.

[11] Patent Number: 5,139,480
[45] Date of Patent: Aug. 18, 1992

[54] NECKING STENTS

[75] Inventors: Randall S. Hickle; Harry W. Parker, both of Lubbock, Tex.

[73] Assignee: BioTech Laboratories, Inc., Lubbock, Tex.

[21] Appl. No.: 570,907

[22] Filed: Aug. 22, 1990

[51] Int. Cl.⁵ .............................................. A61F 2/04
[52] U.S. Cl. ........................................ 604/8; 606/191; 623/12; 600/36
[58] Field of Search ............................. 604/8–10, 604/96; 600/36; 606/191; 623/1, 12

[56] References Cited

U.S. PATENT DOCUMENTS

| | | | |
|---|---|---|---|
| 4,434,797 | 3/1984 | Silander | 606/191 |
| 4,655,771 | 4/1987 | Wallsten | 623/1 |
| 4,729,766 | 3/1988 | Bergentz et al. | 623/1 |
| 4,739,762 | 4/1988 | Palmaz | 604/96 |
| 4,878,906 | 11/1989 | Lindenmann et al. | 623/1 |
| 4,954,126 | 9/1990 | Wallsten | 623/1 X |
| 4,955,899 | 9/1990 | Della Corna et al. | 623/1 |

Primary Examiner—Robert A. Hafer
Assistant Examiner—Kerry Owens
Attorney, Agent, or Firm—Wendell Coffee

[57] ABSTRACT

A stent is made from a thermoplastic material having a glass transition temperature below the normal temperature of the human body. Therefore the thermoplastic polymer may be necked in situ. The stent is made with a series of circumferential strips.

20 Claims, 4 Drawing Sheets

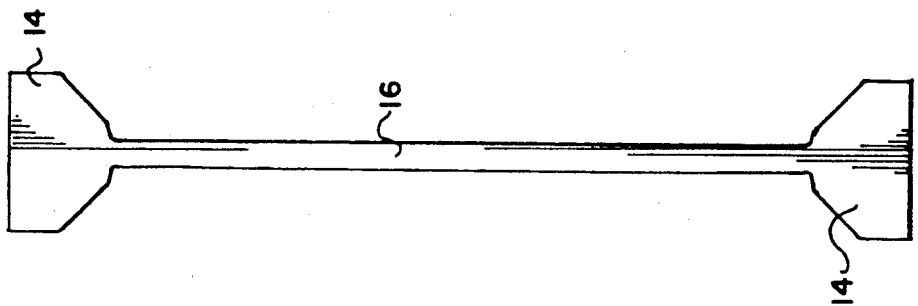
FIG-1-D PRIOR ART
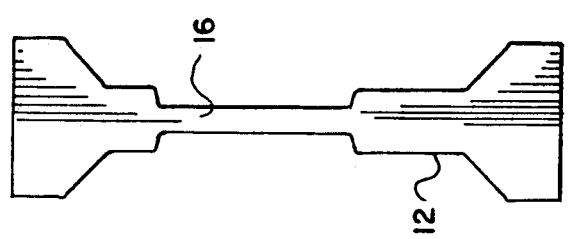
FIG-1-C PRIOR ART
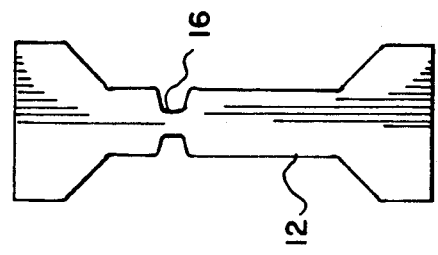
FIG-1-B PRIOR ART
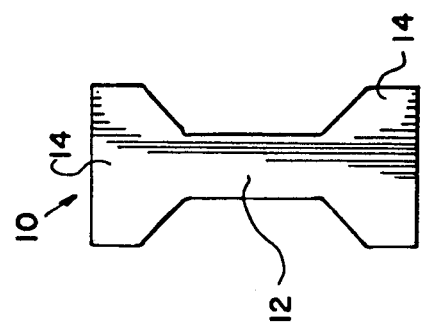
FIG-1-A PRIOR ART

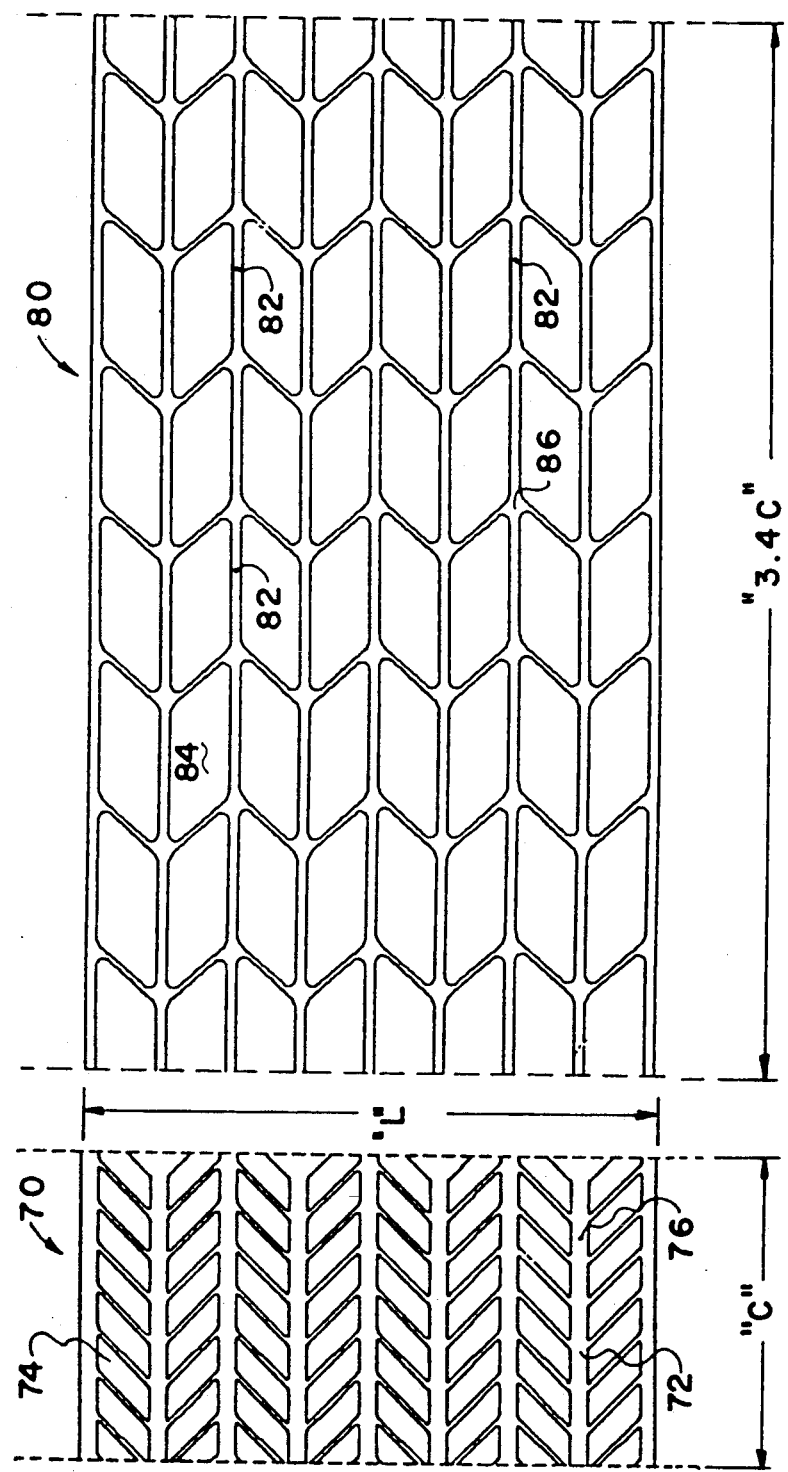

NECKING STENTS

RIGHTS TO INVENTIONS UNDER FEDERAL RESEARCH;

There was no federally sponsored research and development concerning this invention.

BACKGROUND OF THE INVENTION:

(1) Field of the Invention

This invention relates to stents also known as expandable intraluminal grafts for use within a body passageway or duct.

(2) Description of the Related Art

Stents have become the object activity in recent years. Particular reference is made to the patent to PALMAZ, Patent Number 4,733,665, issued on Mar. 29, 1988, and the U.S. Patents, foreign patents and other publications referenced therein.

In the prior art, metals have been the primary material from which stents were made. Some workers in the field, for example, PALMAZ in his patent 4,733,665 has indicated that "any suitable plastic material having the required characteristics previously described" are suitable. Column 6 line 27. Those stents available commercially on the market and about which many research papers have been written, have almost exclusively been of metal.

Trouble has been experienced with some of the stents. It is believed that turbulence of fluid flowing through the stents is one of the problems. According to the stents illustrated in PALMAZ'665, some of them are from woven wires whereas at wire intersections there is a certain amount of irregularity that causes turbulence. Also, when a slotted stent is expanded the bands of metal are twisted in the expansion process so that they project into the lumen somewhat. Also as PALMAZ shows, in both cases the expansion process will reduce the length of the stent.

Obviously the metal stent is quite rigid in comparison to the passageways or ducts. This rigidity in comparison to the more flexible body tissues is in itself an incompatibility which may cause adverse reactions of the body against the foreign material introduced as a stent.

In addition the metals are incompatible in the way enzymes and endothelia react therewith. In particular, metal stents have been associated with the process of neointimal hyperplasia, the excessive overgrowth of intimal endothelial cells that grow to cover the stent's surface. This process of neointimal hyperplasia has been shown to cause restenosis of stents in some cases.

Before this invention it was known that the thermoplastic polymers, above their glass transition temperature, can be elongated or stretched 200 to 500% of their original length before breaking. Elongation increases both the tensile strength and the modulus of the polymer. This phenomena is generally known as necking. This is illustrated in FIGS. 1-A, 1-B, 1-C, and 1-D, wherein a test specimen is subject to increasing stress. First, when a test specimen having a uniform test coupon area, as shown in FIG. 1-A, is elongated there will be an area of yield with a plastic deformation and a corresponding reduction of area. (FIG. 1-B) This area will reduce to a definite amount and then continued stress will not result in a continued reduction of area of the neck but will bring continuing material from the coupon or test area into the neck (FIG. 1-C) until the entire specimen portion is of a reduced area. This is shown in FIG. 1-D. At this point, additional strain will result in a rupture of the neck without significant reduction in cross-sectional area.

This phenomena is described in detail by McCrum, N. G., C. P. Buckley, & C. B. Bucknall, "Principles of Polymer Engineering," pp. 168-172, Oxford University Press, Oxford, (1988).

SUMMARY OF THE INVENTION (1) Progressive Contribution to the Art

This invention takes advantage of the peculiar necking properties of thermoplastic polymers above their glass transition temperature to make stents thereof. A stent may be formed so that the stent may be expanded to as much as four or five times its diameter without changing its length by using these properties. Also, although the stent would of necessity have sufficient "hoop" strength to maintain the lumen in an open condition, it would have flexibility sufficient to be mechanically compatible to the body duct or vessel into which it was inserted. Also, inasmuch as such a large expansion is available, stents may be designed without any change in length. This is readily accomplished by having circumferential slots forming circumferential coupons rather than axial slots which result in a twisting of the individual portions of the stent when it is expanded to a greatly increased diameter.

Some polymers which are useful include polyethylene, polypropylene, polyacrylonitrile, polyehylene terephthalate, and polybutylene terephthalate.

(2) Objects of this Invention

An object of this invention is to provide a stent for body passageways, and more particularly for blood vessels.

Further objects are to achieve the above with devices that are sturdy, compact, durable, simple, safe, efficient, versatile, biologically compatible, long lasting, and reliable, yet inexpensive and easy to manufacture and administer.

The specific nature of the invention, as well as other objects, uses, and advantages thereof, will clearly appear from the following description and from the accompanying drawings, the different views of which are not necessarily scale drawings.

BRIEF DESCRIPTION OF THE DRAWINGS

FIG. 1-A, 1-B, 1-C, and 1-D, are prior art representations showing the necking phenomena of strips or coupons of thermoplastic material.

FIG. 7 is a development of a third embodiment of a stent before expansion.

FIG. 8 is a developed surface of the stent of FIG. 7, showing the surface after it has been expanded about 3.5 times the original size.

As an aid to correlating the terms of the claims to the exemplary drawings, the following catalog of elements and steps is provided:

| | |
|---|---|
| 10 | coupon |
| 12 | strip |
| 14 | tab |
| 16 | neck |
| 20, 30, 50, 60, 70, 80, | stent |
| 22, 32, 52, 62, 72, 82, | strip |
| 24, 34, 54, 64, 74, 84, | hole or slot |
| 26, 36, 56, 66, 76, 86, | tab |

DESCRIPTION OF THE PREFERRED EMBODIMENTS(S)

As discussed in the introduction above, the necking phenomena is known. FIG. 1-A shows an original coupon or specimen 10 having strip 12 of material between the two end tabs 14. As stress is applied to the strip above the yield strength of the material, it will begin to neck as seen in FIG. 1-B with the strip 12 having neck 16. Continued strain upon the material will cause the neck 16 to elongate as seen in FIG. 1-C as is known. Ultimately the entire strip 12 may become the neck 16 as it exists between the two end tabs 14.

The material that is used for this invention is a material which is compatible to human blood, resistant to the formation of blood clot, is conducive to the adherence of endothelia, and has a maximum fractional cross-sectional area after necking of at least 0.5, however, it is preferable that it be a maximum of 0.33. Also it is desirable that the material would have a minimum tensile strength after necking of 15 MPa but preferable that it have a minimum tensile strength after necking of 25 MPa. Likewise it is desirable that it would have a yield strength after necking of at least 10 MPa but it is preferable that it have a yield strength after necking of at least 15 MPa. Also, it is desirable that it have a glass transition temperature between 5 degrees and 39 degrees Celsius, however, it is preferable that it have a glass transition temperature between 20 degrees and 35 degrees Celsius.

Specifically, the following polymers can be produced meeting these requirements: polyethylene, polypropylene, polyacrylonitrile, polyehylene terephthalate, and polybutylene terephthalate. Other polymers also meet these requirements.

The original sheet material of 0.5mm is considered to be suitable. It is highly desirable, after necking, the specimens or neck 16 would have a thickness of no more than 0.5mm. It will be understood that during the necking process not only the width of the strip is reduced but also the thickness.

Figure 2:
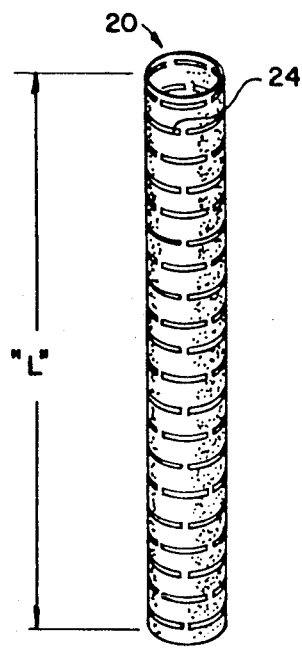
FIG. 2 is a representation of a sheet of thermoplastic material according to this invention which is formed into a stent before its expansion within the lumen.

The sheet material is formed into a tubular configuration as shown in FIG. 2 which is indicated to be an unstressed unexpanded stent 20. The stent of FIG. 2 will have a plurality of circumferential slots 24 therein. As illustrated, there would be twenty (20) rows of slots, each row having four slots therein. i.e., each slot 24 would be approximately one quadrant or slightly less than ¼ the circumference of the stent 20 as illustrated. The rows of slots are staggered as particularly shown in the drawings of FIG. 3. The slots are very narrow before necking, leaving substantial strips 22 between the slots.

Figure 3:
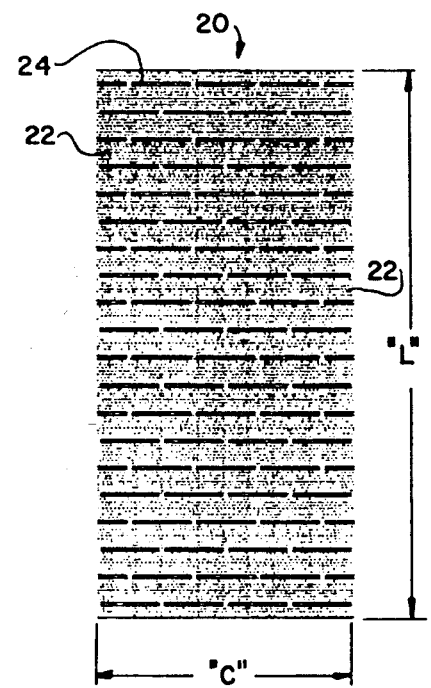
FIG. 3 is a development of the stent of FIG. 2 showing the tubular surface as a flat surface before expansion.
Figure 4:
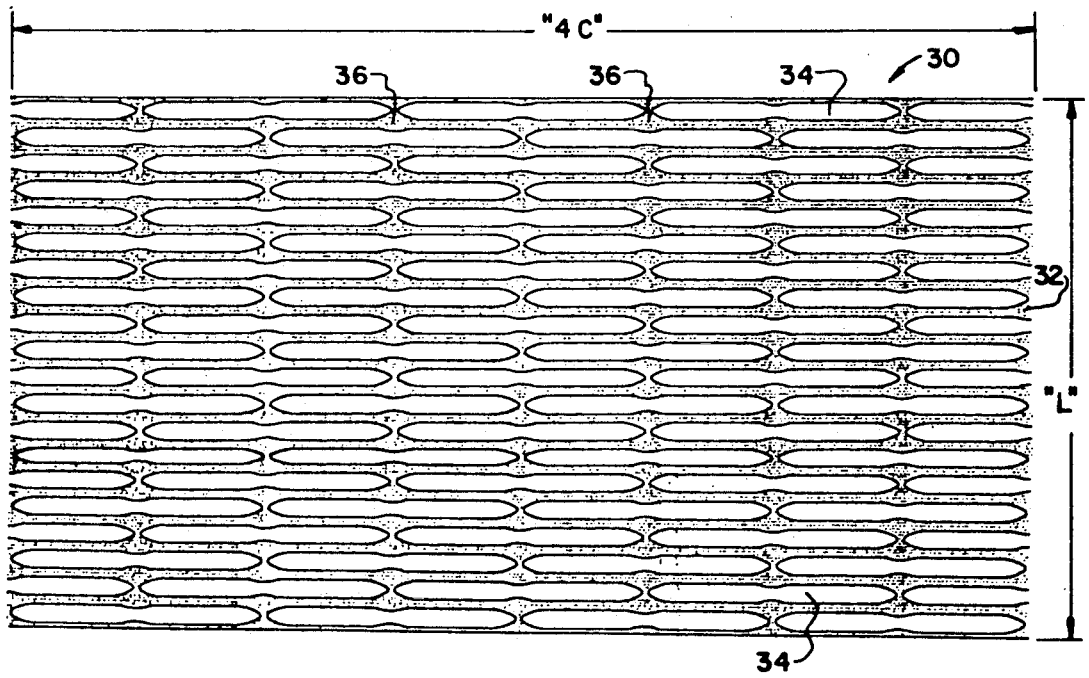
FIG. 4 is a developed surface of the stent of FIG. 2 showing the sheet material after it has been expanded to four times the diameter as that shown in FIG. 3.

FIG. 4 shows the developed surface of stent 30 after it having being expanded to about 4 times the original diameter (FIG. 2), and therefore the circumference would also be 4 times the original circumference (FIG. 3). It may be seen that the original stent 20 before necking has a length of "L" and a circumference of "C". Also, after the stent 30 has been expanded within the lumen it will still have approximately the same length "L" as before, however, the circumference will be 4 times the original circumference as shown in FIG. 4.

The expanded stent 30 will have the same four rows of slots 34. However, as may be seen, after expansion the strips 32 have necked to be over 4 times their original length will have a cross-sectional area of less than 0.25 times their original cross-sectional area. It is noted that individual strips 32 expand more than the stent 30 expands. This is because the material 36 between each of the series of slots is in effect, a tab 36 much the same as the tabs 14 illustrated in FIGS. 1-A-D. Therefore the tab area 36 does not neck and for the entire stent to become 4 times the original circumference it is necessary that the strips 32 which do neck, neck more to compensate for the non-necking "tab" material 36.

It is considered for any successful stent, that the maximum fractional cross-sectional area after necking be at least 0.5 and it is desirable, as stated above that it be preferable that it be a maximum fractional cross-sectional area of 0.33 times the area before necking. It is stated in the above example that the cross-sectional area after necking has a fractional cross-sectional area of less than 0.25.

Figure 5:
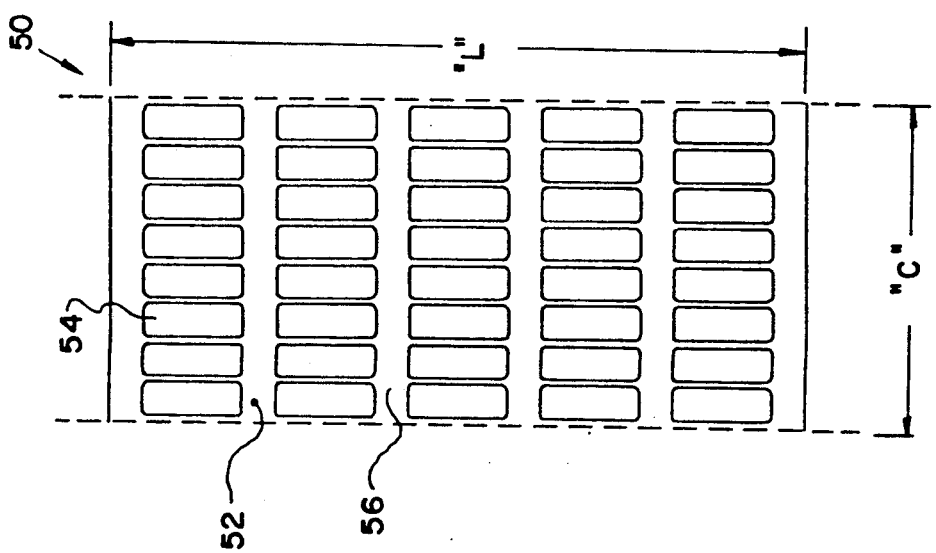
FIG. 5 is a development of a second embodiment of a stent before expansion.

Referring to FIG. 5, there may be seen developed stent 50 that has a certain circumference "C" and also a certain length "L". In this case the holes or slots 54 of the stent 50 are longer in an axial direction or lengthwise direction than they are in a circumferential direction. The slots are such as to leave bands of strips 52 extending circumferentially around the stent. As may be seen, there might be considered to be 4 circumferential bands between the slots 54 and one on each end for a total of 6 bands. Each band has evenly spaced strips 52 separated by tabs 56 as seen. The strips 52 have uniform width and the tabs 56 are wider than the strips. Also the tabs 56 of one band are connected by divisions between slots 54 to tabs 56 of the adjacent bands.

Figure 6:
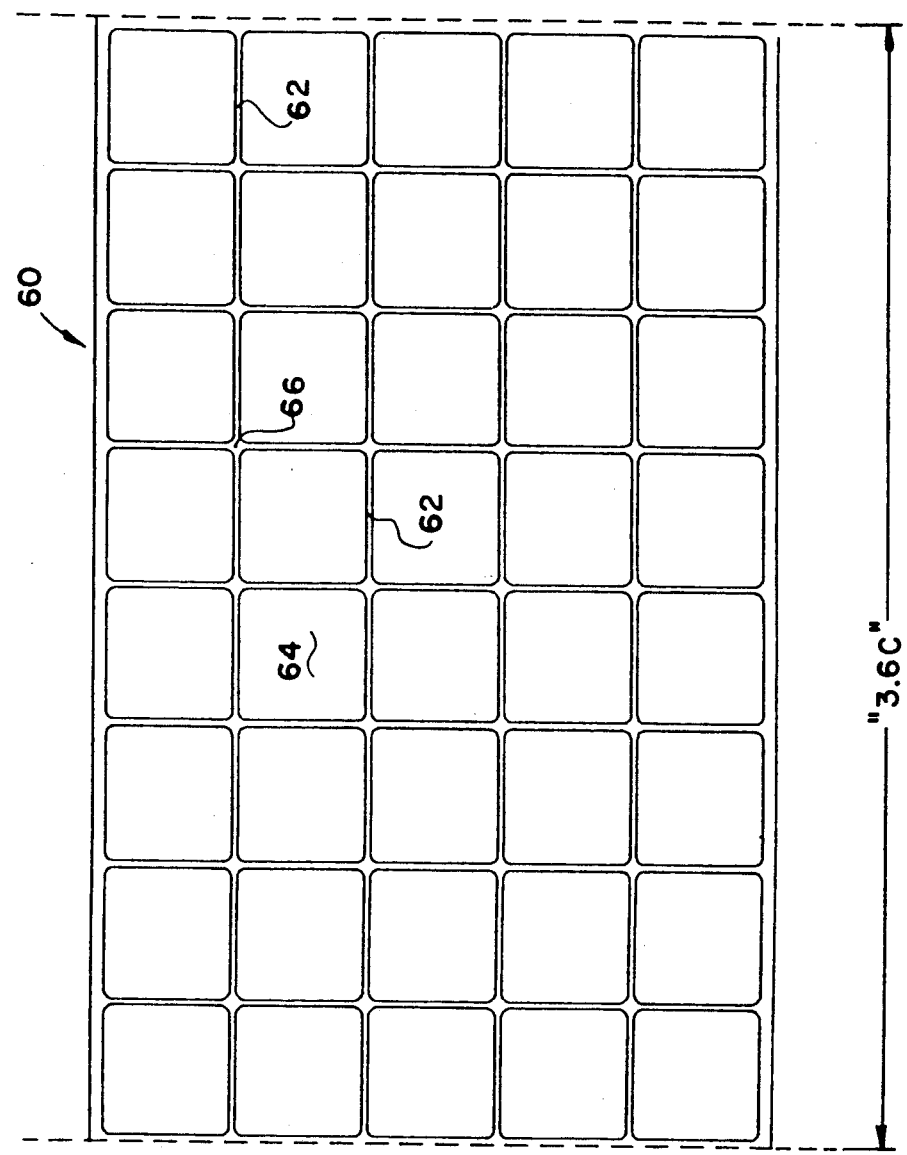
FIG. 6 is a developed surface of the stent of FIG. 5, showing the surface after it has been expanded about 3.5 times the original size.

FIG. 6 discloses stent 60 after expansion of stent 50 of about 3.5 times. Actually it is shown that the circumference of the expanded stent 60 is about 3.6 times the circumference of the unexpanded stent 50. It may be seen that when each of the strips 62 between the different slots 64 have necked they will be quite thin. Also it may be seen that the tabs 66 are still present. In fact the slots 64 will be squares by the time the stent 60 has been expanded. Also it may be seen that each of the strips did expand about 3.5 times, that this would be the cross-sectional area and would be about 0.28 of the cross-sectional area before expansion.

In FIG. 7 there may be seen yet another embodiment of stent 70 before expansion. In this case slots 74 are elongated at an angle. However, it will be recognized that the slots 74 form strips 72 between the slots having tabs 76. The strips, it may be seen, are in circumferential bands as were the strips 22 and 52 in the embodiment of FIG. 3 and FIG. 5.

FIG. 8 shows stent 80 after expansion of the stent 70. Slots 84 after expansion are between bands of strips 82 now necked. The expanded stent 80 has tabs 86 between the expanded strips 82.

It may be seen that although in each case the strips that are necked are in circumferential bands that the slots which define the strips may be circumferentially oriented as in FIG. 3, axially oriented as in FIG. 5, or of some other orientation as in FIG. 8.

Thus it may be seen that we have provided a thermoplastic stent which after expansion within the lumen will have a smooth interior surface and will be free of projections into the lumen. Although it has sufficient strength to hold the lumen at an expanded diameter as one of its functions, it also has a certain amount of flexibility as does the blood vessel itself.

The embodiments shown and described above are only exemplary. We do not claim to have invented all the parts, elements or steps described. Various modifications can be made in the construction, material, arrangement, and operation, and still be within the scope of our invention.

The restrictive description and drawings of the specific examples above do not point out what an infringement of this patent would be, but are to enable one skilled in the art to make and use the invention. The limits of the invention and the bounds of the patent protection are measured by and defined in the following claims.

We claim as our invention:

1. A stent comprising:
   a. a tube formed of unexpanded polymer sheet
   b. a plurality of holes through the sheet,
   c. said polymer sheet being a thermoplastic having
      i. a glass transition temperature between 5 degrees and 39 degrees Celsius,
      ii. a minimum tensile strength after necking of 15 MPa,
      iii. a minimum yield strength after necking of 10 MPa,
      iv. a maximum fractional cross-sectional area after necking of 0.5, and
      v. a compatibility with human body fluids.

2. The invention as defined in claim 1 further comprising said maximum fractional cross-sectional area after necking is 0.33.

3. The invention as defined in claim 1 wherein said yield strength after necking is at least 15 MPa.

4. The invention as defined in claim 1 wherein said tensile strength after necking is at least 25 MPa.

5. The invention as defined in claim 1 wherein the glass transition temperature is between 20 degrees Celsius and 35 degrees Celsius.

6. The invention as defined in claim 1 wherein said sheet is about 0.5 mm wall thickness before necking.

7. The invention as defined in claim 1 wherein said polymer sheet is made of a material selected from the group of polymers consisting of polyethylene, polypropylene, polyacrylonitrile, polyehylene terephthalate, and polybutylene terephthalate.

8. The invention as defined in claim 1 wherein said holes are uniformly spaced and form circumferential bands with strips between the holes, said strips of uniform width and have tabs of greater width evenly spaced in the band between successive strips.

9. The invention as defined in claim 8 wherein said tabs in each circumferential band are connected to the tabs in the adjacent bands.

10. The invention as defined in claim 1 wherein said stent is for a blood vessel and the sheet material is compatible with blood.

11. The invention as defined in claim 10 wherein said sheet is conducive to endothelialization.

12. The invention as defined in claim 11 further comprising said maximum cross-sectional area after necking is 0.33.

13. The invention as defined in claim 12 wherein said yield strength is at least 15 MPa after necking.

14. The invention as defined in claim 13 wherein said tensile strength is at least 25 MPa after necking.

15. The invention as defined in claim 14 wherein the glass transition temperature is between 20 degrees Celsius and 35 degrees Celsius.

16. The invention as defined in claim 15 wherein said sheet is about 0.5 mm wall thickness before necking.

17. The invention as defined in claim 16 wherein said holes are uniformly spaced and form circumferential bands with strips between the holes, said strips of uniform width and have tabs of greater width evenly spaced in the band between successive strips.

18. The invention as defined in claim 17 wherein said tabs in each circumferential band are connected to the tabs in the adjacent bands.

19. A stent for blood vessels comprising:
   a. a tube formed of an unexpanded polymer sheet having a wall thickness of about 0.5 mm,
   b. a plurality of circumferential bands having strips of uniform width, and said bands having tabs of greater width evenly spaced between the strips,
   c. said polymer sheet being a thermoplastic having
      i. a glass transition temperature between 20 degrees and 35 degrees Celsius,
      ii. a minimum tensile strength after necking of 25 MPa,
      iii. a minimum yield strength after necking of 15 MPa,
      iv. a maximum fractional cross-sectional area after necking of 0.33, and
      v. a compatibility with human blood and being condusive to endothelialization, and
   d. said thermoplastic selected from the group of polymers consisting of polyethylene, polypropylene, polyacrylonitrile, polyehylene terephthalate, and polybutylene terephthalate.

20. The process of inserting a stent into a vessel comprising:
   A. inserting said stent into the vessel, said stent before insertion being
      i. a tube formed of an unexpanded polymer sheet,
      ii. a plurality of holes through the sheet,
      iii. said polymer sheet being a thermoplastic having:
         a. a glass transition temperature between 5 degrees and 39 degrees Celsius,
         b. a minimum tensile strength after necking of 15MPa,
         c. a minimum yield strength after necking of 10MPa,
         d. a maximum fractional cross-sectional area after necking of 0.5, and
         e. a compatibility with human body fluids,
   B. expanding the stent until portions of the sheet forming stent are necked.

* * * * *